(12) United States Patent
Guidi et al.

(10) Patent No.: US 7,018,743 B2
(45) Date of Patent: Mar. 28, 2006

(54) DUAL CHEMISTRY ELECTRODE DESIGN

(75) Inventors: Michael L. Guidi, West Seneca, NY (US); Hong Gan, East Amherst, NY (US); Mark J. Roy, Buffalo, NY (US); Susan L. Clare, East Amherst, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 580 days.

(21) Appl. No.: 10/336,455

(22) Filed: Jan. 2, 2003

(65) Prior Publication Data

US 2003/0129485 A1    Jul. 10, 2003

Related U.S. Application Data

(60) Provisional application No. 60/345,724, filed on Jan. 2, 2002.

(51) Int. Cl.
*H01M 4/02*    (2006.01)
*H01M 4/58*    (2006.01)

(52) U.S. Cl. ............... 429/233; 429/244; 429/231.95; 429/245

(58) Field of Classification Search ............... 429/219, 429/231.5, 245, 231.95, 332, 327, 233, 244, 429/220, 221, 223, 224, 231.1, 231.7, 328, 429/329, 330, 333, 231.3
See application file for complete search history.

(56) References Cited

U.S. PATENT DOCUMENTS

| | | | |
|---|---|---|---|
| 4,310,609 A | 1/1982 | Liang et al. | |
| 5,180,642 A | 1/1993 | Weiss et al. | |
| 5,472,810 A | 12/1995 | Takeuchi et al. | |
| 5,516,340 A | 5/1996 | Takeuchi et al. | |
| 5,744,258 A | 4/1998 | Bai et al. | |
| 6,063,519 A | 5/2000 | Barker et al. | |
| 6,607,861 B1 * | 8/2003 | Gan et al. | 429/219 |
| 2001/0044047 A1 * | 11/2001 | Gan et al. | 429/219 |

* cited by examiner

*Primary Examiner*—Michael Barr
*Assistant Examiner*—Monique Wills
(74) *Attorney, Agent, or Firm*—Michael F. Scalise

(57) ABSTRACT

A new cathode design has a first cathode active material of a relatively low energy density but of a relatively high rate capability contacted to the outer sides of first and second cathode current collectors and a second cathode active material having a relatively high energy density but of a relatively low rate capability in contact with the inner sides of the current collectors. The second cathode active material has a greater peripheral extend than the current collectors and the opposed layers of the first cathode active material between which it is sandwiched. This construction helps prevent delamination by promoting improved contact of the respective active materials to the current collectors. The present cathode design is useful for powering an implantable medical device requiring a high rate discharge application.

25 Claims, 4 Drawing Sheets

DUAL CHEMISTRY ELECTRODE DESIGN

CROSS-REFERENCE TO RELATED APPLICATION

This application claims priority based on provisional application Ser. No. 60/345,724, filed Jan. 2, 2002.

BACKGROUND OF THE INVENTION

1. Field of Invention

This invention relates to the conversion of chemical energy to electrical energy. In particular, the present invention relates to an electrode design having a cathode active material of a relatively low energy density but of a relatively high rate capability and a second active material having a relatively high energy density but of a relatively low rate capability. The first and second active materials are short circuited to each other by contacting the opposite sides of a current collector. A preferred form of the cell has the electrode as a cathode connected to a terminal lead insulated from the casing serving as the negative terminal for the anode electrode. The present electrode design is useful for powering an implantable medical device requiring a high rate discharge application.

2. Prior Art

As is well known by those skilled in the art, an implantable cardiac defibrillator is a device that requires a power source for a generally medium rate, constant resistance load component provided by circuits performing such functions as, for example, the heart sensing and pacing functions. From time-to-time, the cardiac defibrillator may require a generally high rate, pulse discharge load component that occurs, for example, during charging of a capacitor in the defibrillator for the purpose of delivering an electrical shock to the heart to treat tachyarrhythmias, the irregular, rapid heartbeats that can be fatal if left uncorrected.

It is generally recognized that for lithium cells, silver vanadium oxide (SVO) and, in particular, $\epsilon$-phase silver vanadium oxide ($AgV_2O_{5.5}$), is preferred as the cathode active material. This active material has a theoretical volumetric capacity of 1.37 Ah/ml. By comparison, the theoretical volumetric capacity of $CF_x$ material (x=1.1) is 2.42 Ah/ml, which is 1.77 times that of $\epsilon$-phase silver vanadium oxide. For powering a cardiac defibrillator, SVO is preferred because it can deliver high current pulses or high energy within a short period of time. Although $CF_x$ has higher volumetric capacity, it cannot be used in medical devices requiring a high rate discharge application due to its low to medium rate of discharge capability.

A novel electrode construction using both a high rate active material, such as SVO, and a high energy density material, such as $CF_x$, is described in U.S. Pat. No. 6,551,747 to Gan. This application is assigned to the assignee of the present invention and incorporated herein by reference. FIG. 1 is a schematic view of a portion of a cathode electrode 10 according to the filed application. Electrode 10 is in an exaggerated, uncompressed condition and comprises spaced apart current collectors 12 and 14 supporting layers 16 and 18 of a first cathode active material on their respective outer major sides. The first cathode active materials 16, 18 are of a relatively high rate capability, but of a low energy density in comparison to a second cathode active material 20 sandwiched between and in contact with the current collectors 12, 14.

More particularly, the cathode active layer 16 has upper and lower sides 16A and 16B extending to and meeting with spaced apart left and right ends 16C and 16D. While not shown in the drawing, the sides 16A, 16B and ends 16C, 16D extend to and meet with a front side and a back side. Similarly, the cathode active layer 18 has lower and upper sides 18A and 18B and ends 18C and 18D extending to and meeting with a front side and a back side. For all intents and purposes, the layers 16 and 18 are of a similar shape.

The intermediate cathode active layer 20 has upper and lower sides 20A and 20B extending to spaced apart left and right ends 20C and 20D. The sides 20A, 20B and the ends 20C, 20D extend to and meet with a front side and a back side.

In an electrochemical cell (not shown), the first cathode active layers 16, 18 supported on the current collectors 12, 14, in turn, sandwiching the intermediate second cathode active layer 20 is compressed into a relatively thin assembly. In the compressed state, the ends 16C and 18C of the cathode layers 16, 18 extend beyond the ends 20C and 20D of the second active material layer 20. However, in the compressed state the ends 16C and 18 do not touch each other. While not shown, the front and back sides of the layers 16 and 18 also extend beyond the front and back sides of the intermediate layer 20, but in the compressed state they also do not touch each other. In the compressed state, the distal ends of the current collectors 12, 14 generally align with the left edge 20C of the intermediate layer 20.

With the cathode 10 shown in FIG. 1, it is possible for the cathode layers 16 and 18 to delaminate from the current collectors 12 and 14, especially in the vicinity of the ends 16C and 18C and the front and back sides. Essentially, potential sites of delamination exist wherever the layers 16, 18 extend beyond the peripheral edge of the intermediate layer 20 and of the current collectors 12, 14. The electrode construction of the present invention prevents such delamination from occurring.

SUMMARY OF THE INVENTION

Accordingly, the object of the present invention is to improve the performance of lithium electrochemical cells by providing a new concept in electrode design. This new design is predicated on the optimization of the relatively high rate capability of SVO contacted to one side of a current collector with the relatively high energy density of $CF_x$ contacted to the other side of the current collector. This design has the separate SVO and $CF_x$ materials short-circuited to each other through the current collector. Providing the active materials in a short circuit relationship means that their respective attributes of high rate and high energy density benefit overall cell discharge performance. Further, the present invention provides a construction for the respective active materials that promotes improved contact with the opposed sides of the current collector. This, in turn, prevents delamination of the active materials from the current collector. Delamination can result in diminished discharge efficiency.

These and other objects of the present invention will become increasingly more apparent to those skilled in the art by reference to the following description and to the appended drawings.

DETAILED DESCRIPTION OF THE PREFERRED EMBODIMENTS

Figure 1:
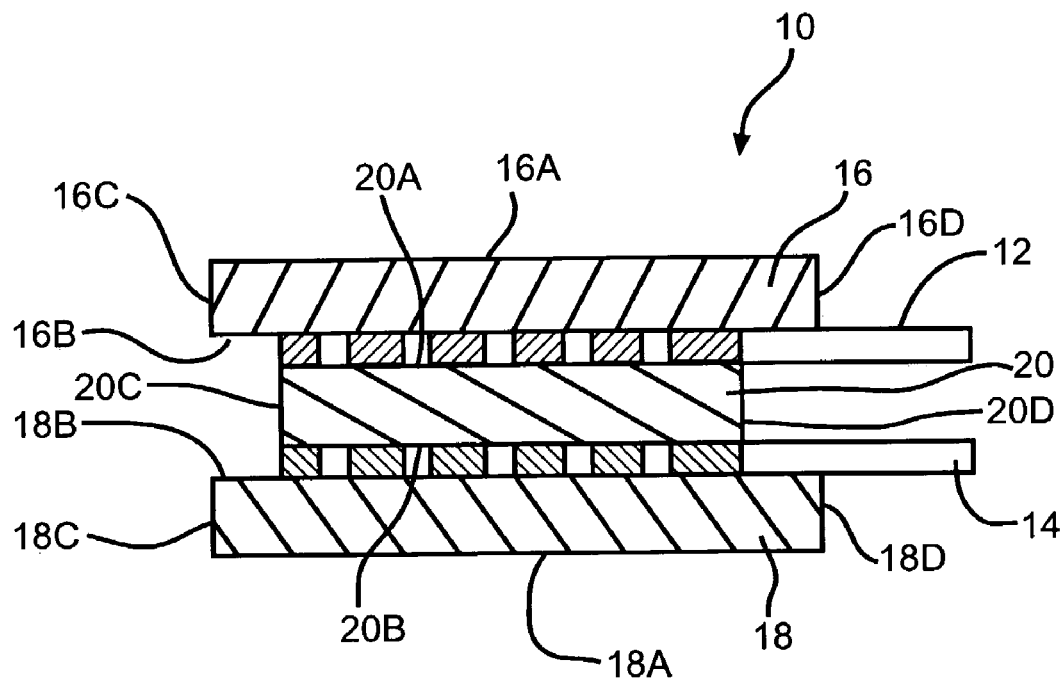
FIG. 1 is a schematic of a prior art cathode 10 of a high energy density cathode material 20 sandwiched between two current collectors 12, 14 and two layers of a high rate cathode material 16 and 18.

As used herein, the term "pulse" means a short burst of electrical current of significantly greater amplitude than that of a pre-pulse current immediately prior to the pulse. A pulse train consists of at least two pulses of electrical current delivered in relatively short succession with or without open circuit rest between the pulses. An exemplary pulse train may consist of four 10-second pulses (23.2 mA/cm$^2$) with a 15 second rest between each pulse. A typically used range of current densities for cells powering implantable medical devices is from about 15 mA/cm$^2$ to about 50 mA/cm$^2$, and more preferably from about 18 mA/cm$^2$ to about 35 mA/cm$^2$. Typically, a 10 second pulse is suitable for medical implantable applications. However, it could be significantly shorter or longer depending on the specific cell design and chemistry.

An electrochemical cell that possesses sufficient energy density and discharge capacity required to meet the vigorous requirements of implantable medical devices comprises an anode of a metal selected from Groups IA, IIA and IIIB of the Periodic Table of the Elements. Such anode active materials include lithium, sodium, potassium, etc., and their alloys and intermetallic compounds including, for example, Li—Si, Li—Al, Li—B and Li—Si—B alloys and intermetallic compounds. The preferred anode comprises lithium. An alternate anode comprises a lithium alloy such as a lithium-aluminum alloy. The greater the amounts of aluminum present by weight in the alloy, however, the lower the energy density of the cell.

The form of the anode may vary, but preferably the anode is a thin metal sheet or foil of the anode metal, pressed or rolled on a metallic anode current collector, i.e., preferably comprising titanium, titanium alloy or nickel, to form an anode component. Copper, tungsten and tantalum are also suitable materials for the anode current collector. In the exemplary cell of the present invention, the anode component has an extended tab or lead of the same material as the anode current collector, i.e., preferably nickel or titanium, integrally formed therewith such as by welding and contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell of the present invention further comprises a cathode of electrically conductive material that serves as the other electrode of the cell. The cathode is preferably of solid materials and the electrochemical reaction at the cathode involves conversion of ions that migrate from the anode to the cathode into atomic or molecular forms. The solid cathode may comprise a first active material of a metal element, a metal oxide, a mixed metal oxide and a metal sulfide, and combinations thereof and a second active material of a carbonaceous chemistry. The metal oxide, the mixed metal oxide and the metal sulfide of the first active material has a relatively lower energy density but a relatively higher rate capability than the second active material.

The first active material is formed by the chemical addition, reaction, or otherwise intimate contact of various metal oxides, metal sulfides and/or metal elements, preferably during thermal treatment, sol-gel formation, chemical vapor deposition or hydrothermal synthesis in mixed states. The active materials thereby produced contain metals, oxides and sulfides of Groups, IB, IIB, IIIB, IVB, VB, VIB, VIIB and VIII, which includes the noble metals and/or other oxide and sulfide compounds. A preferred cathode active material is a reaction product of at least silver and vanadium.

One preferred mixed metal oxide is a transition metal oxide having the general formula $SM_xV_2O_y$, where SM is a metal selected from Groups IB to VIIB and VIII of the Periodic Table of Elements, wherein x is about 0.30 to 2.0 and y is about 4.5 to 6.0 in the general formula. By way of illustration, and in no way intended to be limiting, one exemplary cathode active material comprises silver vanadium oxide having the general formula $Ag_xV_2O_y$, in any one of its many phases, i.e., β-phase silver vanadium oxide having in the general formula x=0.35 and y=5.8, γ-phase silver vanadium oxide having in the general formula x=0.74 and y=5.37 and ε-phase silver vanadium oxide having in the general formula x=1.0 and y=5.5, and combination and mixtures of phases thereof. For a more detailed description of such cathode active materials reference U.S. Pat. No. 4,310,609 to Liang et al., which is assigned to the assignee of the present invention and incorporated herein by reference.

Another preferred composite transition metal oxide cathode material includes $V_2O_z$ wherein z≦5 combined with $Ag_2O$ with silver in either the silver (II), silver (I) or silver (0) oxidation state and CuO with copper in either the copper (II), copper (I) or copper (0) oxidation state to provide the mixed metal oxide having the general formula $Cu_xAg_yV_2O_z$, (CSVO). Thus, the composite cathode active material may be described as a metal oxide-metal oxide-metal oxide, a metal-metal oxide-metal oxide, or a metal-metal-metal oxide and the range of material compositions found for $Cu_xAg_yV_2O_z$ is preferably about 0.01≦z≦6.5. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material reference is made to U.S. Pat. Nos. 5,472,810 to Takeuchi et al. and 5,516,340 to Takeuchi et al., both of which are assigned to the assignee of the present invention and incorporated herein by reference.

The cathode design of the present invention further includes a second active material of a relatively high energy density and a relatively low rate capability in comparison to the first cathode active material. The second active material is preferably a carbonaceous compound prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.2 and 1.2, and $(C_2F)_n$ wherein the n refers to the number of monomer units which can vary widely. The true density of $CF_x$ is 2.70 g/ml and its theoretical capacity is 2.42 Ah/ml.

In a broader sense, it is contemplated by the scope of the present invention that the first cathode active material is any material that has a relatively lower energy density but a relatively higher rate capability than the second active material. In addition to silver vanadium oxide and copper silver vanadium oxide, $V_2O_5$, $MnO_2$, $LiCoO_2$, $LiNiO_2$, $LiMn_2O_4$, $TiS_2$, $Cu_2S$, FeS, $FeS_2$, copper oxide, copper vanadium oxide, and mixtures thereof are useful as the first active material. And, in addition to fluorinated carbon, $Ag_2O$, $Ag_2O_2$, CuF, $Ag_2CrO_4$, $MnO_2$, and even SVO itself, are useful as the second active material. The theoretical volumetric capacity (Ah/ml) of $CF_x$ is 2.42, $Ag_2O_2$ is 3.24, $Ag_2O$ is 1.65 and $AgV_2O_{5.5}$ is 1.37. Thus, $CF_x$, $Ag_2O_2$, $Ag_2O$, all have higher theoretical volumetric capacities than that of SVO.

Before fabrication into an electrode structure for incorporation into an electrochemical cell according to the present invention, the first cathode active material prepared as described above is preferably mixed with a binder material such as a powdered fluoro-polymer, more preferably powdered polytetrafluoroethylene or powdered polyvinylidene flouride present at about 1 to about 5 weight percent of the cathode mixture. Further, up to about 10 weight percent of a conductive diluent is preferably added to the first cathode mixture to improve conductivity. Suitable materials for this purpose include acetylene black, carbon black and/or graphite or a metallic powder such as powdered nickel, aluminum, titanium and stainless steel. The preferred first cathode active mixture thus includes a powdered fluoro-polymer binder present at about 3 weight percent, a conductive diluent present at about 3 weight percent and about 94 weight percent of the cathode active material.

The second cathode active mixture includes a powdered fluoro-polymer binder present at about 4 weight percent, a conductive diluent present at about 5 weight percent and about 91 weight percent of the cathode active material. A preferred second active mixture is, by weight, 91% $CF_x$, 4% PTFE and 5% carbon black.

Cathode components for incorporation into an electrochemical cell according to the present invention may be prepared by rolling, spreading or pressing the first and second cathode active materials onto a suitable current collector selected from the group consisting of stainless steel, titanium, tantalum, platinum and gold. The preferred current collector material is titanium, and most preferably the titanium cathode current collector has a thin layer of graphite/carbon paint applied thereto. Cathodes prepared as described above may be in the form of one or more plates operatively associated with at least one or more plates of anode material, or in the form of a strip wound with a corresponding strip of anode material in a structure similar to a "jellyroll".

Figure 2:
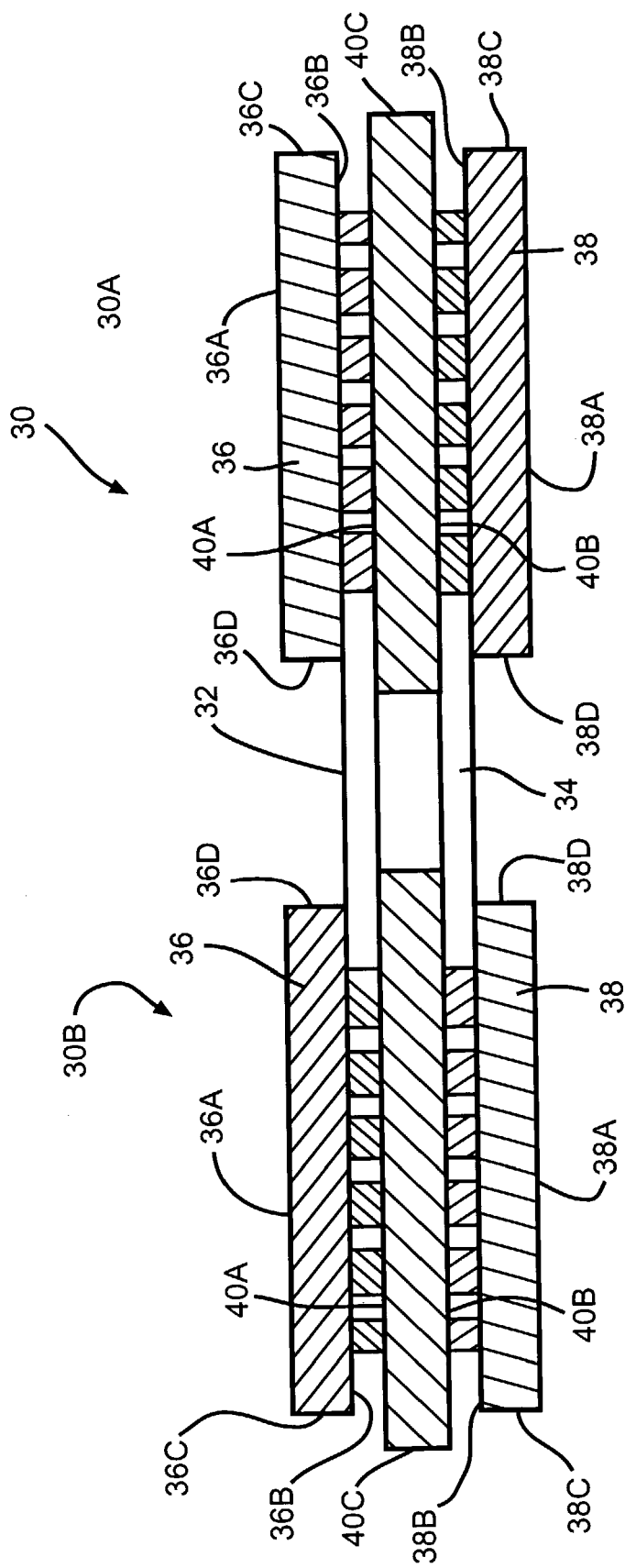
FIG. 2 is a schematic of an exemplary embodiment of a cathode 30 according to the present invention having a high energy density cathode material 40 of a greater peripheral extent than current collectors 32, 34 and layers of a high rate cathode material 36 and 38 between which it is sandwiched.

FIG. 2 is a schematic view of the present invention cathode electrode 30 in an exaggerated, uncompressed condition. Electrode 30 comprises opposed assemblies 30A and 30B extending outwardly from the opposite sides of current collectors 32 and 34. This leaves an intermediate portion of the current collectors 32 and 34 that are not contacted by either the first or the second cathode active materials. The cathode assemblies 30A and 30B are essentially identical and will be described with respect to one of them.

Cathode assembly 30A in an exaggerated, uncompressed condition comprises spaced apart current collectors 32 and 34 supporting layers 36 and 38 of a first cathode active material on their respective outer major sides. As with the prior art electrode 10, the first cathode active materials 36, 38 are of a relatively high rate capability, but of a low energy density in comparison to a second cathode active material 40 sandwiched between and in contact with the current collectors 32, 34.

More particularly, the cathode active layer 36 has upper and lower sides 36A and 36B extending to and meeting with spaced apart left and right ends 36C and 36D. While not shown in FIG. 2, the sides 36A, 36B and ends 36C, 36D extend to a front side and a back side. Similarly, the cathode active layer 38 has lower and upper sides 38A and 38B and ends 38C and 38D extending to a front side and a back side. For all intents and purposes, the layers 36 and 38 are of a similar shape.

The intermediate cathode active layer 40 has upper and lower sides 40A and 40B extending to spaced apart left and right ends 40C and 40D. The sides 40A, 40B and the ends 40C, 40D extend to a front side and a back side. The end 40C of the intermediate, second active material cathode layer 40 extends beyond the ends 36C and 38C of the first active material cathode layers 36, 38. Similarly, the end 40D of layer 40 extends beyond the ends 36D and 38D of the cathode layers 36, 38. While not shown, the front and back sides of the intermediate layer extend beyond the front and back sides of the layers 36 and 38.

Figure 3:
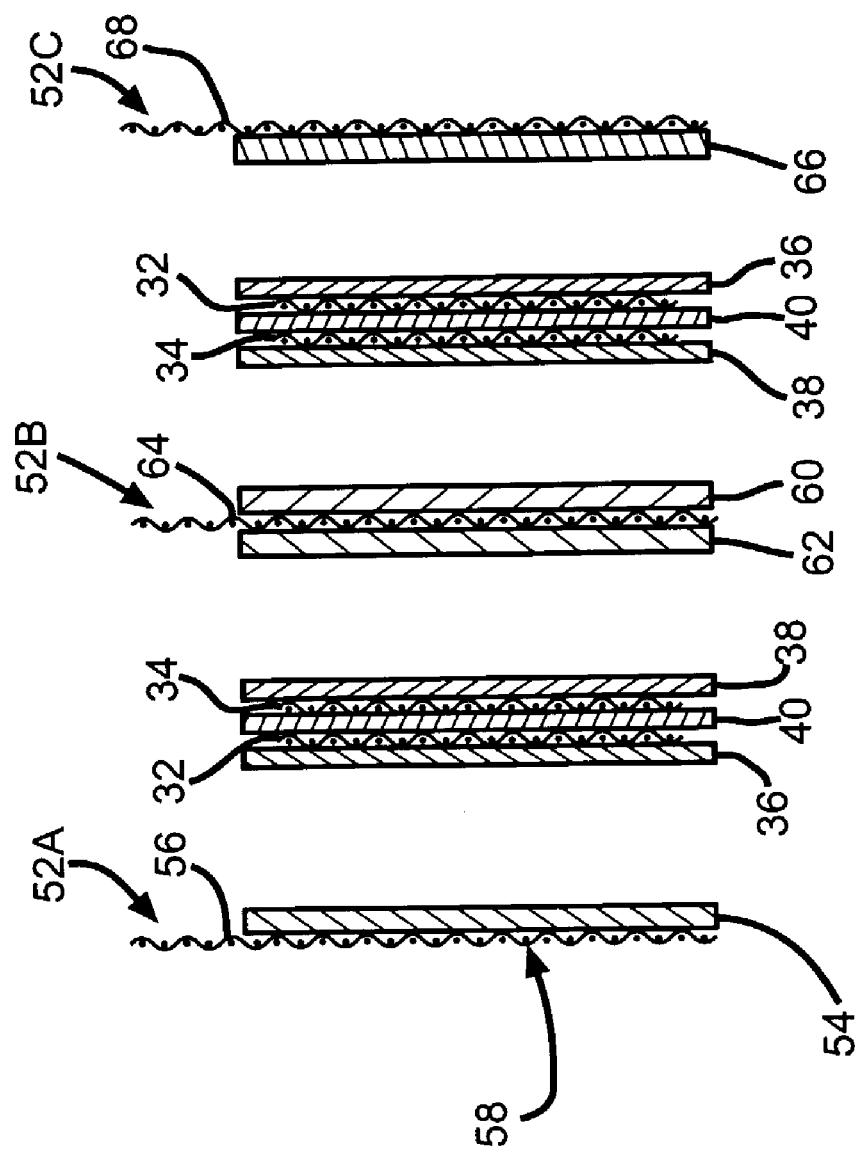
FIG. 3 is a schematic of one embodiment of an exemplary electrochemical cell 50 including the cathode 30 shown in FIG. 2.

As shown in FIG. 3, the cathode assemblies 30A and 30B are folded toward each other and toward the opposed sides of an anode electrode to provide an electrochemical cell. However, before the assemblies 30A and 30B are folded, they are compressed. This causes the periphery of the first cathode active materials 36, 38 to expand substantially to the size of the periphery of the second cathode material 40. There is also some expansion of the second active material during compression of the assemblies, just not as much as that of the first active material.

Also, while not shown in the drawing, the active materials 36, 38 and 40 touch at their peripheries beyond the current collector 32 and 34 with the peripheries being substantially aligned. The assemblies are compressed in a fixture with the fixture wall governing the amount of expansion of the first active materials. In the compressed state, the thickness of each cathode assembly is from about 0.020 inches to about 0.035 inches, the current collectors 32, 34 each being about 0.002 inches thick with a carbon coating of about 0.0004 inches thick per current collector side.

In the present invention cathode 30, the provision of the peripheral edge of the intermediate layer 40 extending beyond the peripheral edges of the layers 36 and 38 in the uncompressed state prevents delamination of the first cathode active material from the current collectors 32 and 34 after the assembly is pressed to its final thickness. In other words, providing the peripheral edge of the intermediate cathode layer 40 extending beyond the peripheral edges of the current collectors 32 and 34 and of the first active layers 36 and 38 ensures that delamination of the compressed cathode does not occur when the assemblies 30A and 30B are folded toward each other and electrically associated with the anode electrode.

The anode electrode comprises a number of anode structures; each comprising a current collector having an alkali metal contacted thereto, lithium being preferred. In this embodiment, there are three anode structures 52A, 52B and 52C disposed adjacent to at least one of the cathode assemblies 30A and 30B.

More particularly, the cell 50 is built with the first anode structure 52A having lithium 54 only contacted to the one major side of the anode current collector 56 adjacent to the cathode assembly 30B. The opposite major side 58 of the anode current collector 56 is bare and in direct contact with the casing serving as the anode electrode terminal in the case-negative cell design. The second anode structure 52B is intermediate the cathode assemblies 30A, 30B and comprises layers 60 and 62 of lithium contacted to the opposed major sides of current collector 64. The third anode structure 52C comprises lithium 66 only contacted to the one major side of the anode current collector 68 adjacent to the cathode assembly 30A. The anode layers 54, 60, 62 and 66 are of substantially the same size and thickness.

The cathode current collectors 32 and 34 are connected to a common terminal insulated from the casing by a suitable glass-to-metal seal. This describes a case-negative cell design, which is the preferred form of the cell 50. The cell 50 can also be built in a case-positive design with the cathode current collectors contacted to the casing and the anode current collectors 56, 64 and 68 connected to a common terminal lead insulated from the casing.

In a further embodiment, the cell is built in a case-neutral configuration with both the anode and the cathode being connected to respective terminal leads insulated from the casing. In this embodiment, there is a layer of separator between the anode current collectors 56 and 68 and the casing side wall as well as between each of the electrodes. The separator will be described in detail hereinafter.

Figure 4:
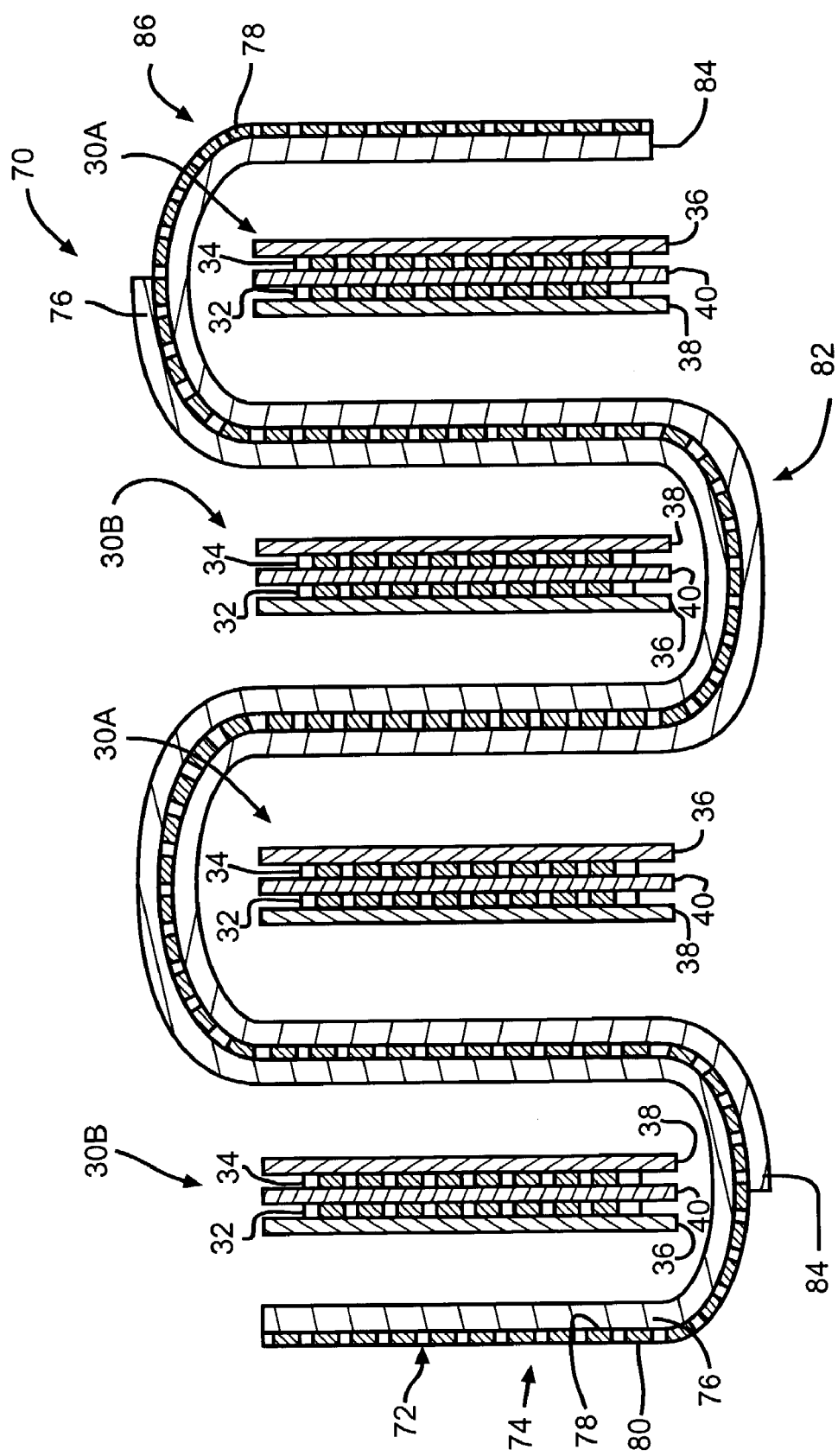
FIG. 4 is a schematic of another embodiment of an exemplary electrochemical cell 70 including the cathode 30 shown in FIG. 2.

FIG. 4 is a schematic view of another electrochemical cell 70 according to the present invention. As with the cell 50 described in FIG. 3, this cell 70 is shown exaggerated somewhat with the first active materials 36 and 38 shown not touching the second active material 40. However, in a compressed state, the active materials 36, 38 and 40 touch at the ends beyond the current collectors 32, 34 with the ends being substantially aligned. Cell 70 is housed in a conductive casing (not shown) in either a case-negative, a case-positive or a case-neutral design.

The anode electrode comprises an anode current collector 72 having an alkali metal contacted thereto. The preferred alkali metal is lithium, and it is provided in a serpentine shape weaving or winding between two pairs of the cathode assemblies 30A and 30B. The cathode assemblies similar in thickness to those described with respect to cell 50.

The cell 70 is built with the anode portion 74 having lithium 76 only contacted to the one major side 78 of the anode current collector 72 adjacent to the cathode assembly 30B. The opposite major side 80 of the anode current collector 72 is bare and in direct contact with the casing serving as the anode electrode terminal in the case-negative cell design. At the bend between the first pair of cathode assemblies 30B and 30A, the serpentine anode electrode doubles back to provide anode portion 82 having the lithium 76 contacting the current collector side 78 and a layer of lithium 84 contacted to the other major side 80 of the current collector. The anode portion 82 continues weaving between the cathode assemblies 30A, 30B, and 30A. At the bend between the second pair of cathode assembly 30B and 30A, the lithium layer 76 ends. Then, the anode electrode is completed by anode portion 86 comprising lithium layer 84 only contacted to the major side 80 of the anode current collector 72. Here, the opposite major side 78 of the anode current collector is bare and in direct contact with the casing serving as the anode electrode terminal. Anode layers 76 and 84 are of substantially the same size and thickness.

In order to prevent internal short circuit conditions, the sandwich cathode is separated from the Group IA, IIA or IIIB anode by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, nonwoven glass, polypropylene, polyethylene, glass fiber materials, ceramics, polytetrafluoroethylene membrane commercially available under the designation ZITEX (Chemplast Inc.), polypropylene/polyethylene membrane commercially available under the designation CELGARD (Celanese Plastic Company, Inc.), a membrane commercially available under the designation DEXIGLAS (C. H. Dexter, Div., Dexter Corp.), and a polyethylene membrane commercially available from Tonen Chemical Corp.

The electrochemical cell of the present invention further includes a nonaqueous, ionically conductive electrolyte that serves as a medium for migration of ions between the anode and the cathode electrodes during the electrochemical reactions of the cell. The electrochemical reaction at the electrodes involves conversion of ions in atomic or molecular forms that migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive salt dissolved in a mixture of aprotic organic solvents comprising a low viscosity solvent and a high permittivity solvent. In the case of an anode comprising lithium, preferred lithium salts that are useful as a vehicle for transport of alkali metal ions from the anode to the cathode include $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, $LiSCN$, $LiO_3SCF_3$, $LiC_6F_5SO_3$, $LiO_2CCF_3$, $LiSO_6F$, $LiB(C_6H_5)_4$ and $LiCF_3SO_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2-methoxyethane (EME), ethyl methyl carbonate, methyl propyl carbonate, ethyl propyl carbonate, diethyl carbonate, dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methylpyrrolidinone (NMP), and mixtures thereof. In the present invention, the preferred anode is lithium metal and the preferred electrolyte is 0.8M to 1.5M $LiAsF_6$ or $LiPF_6$ dissolved in a 50:50 mixture, by volume, of propylene carbonate and 1,2-dimethoxyethane.

According to the present invention, SVO cathode material, which provides a relatively high power or rate capability but a relatively low energy density or volumetric capability and $CF_x$ cathode material, which has a relatively high energy density but a relatively low rate capability, are individually pressed on current collector screens.

Since $CF_x$ material has significantly higher volumetric capacity than that of SVO material, i.e., approximately 1.77 times greater, in order to optimize the final cell capacity, the amount of $CF_x$ material should be maximized and the amount of SVO material used in each electrode should be minimized to the point that it is still practical in engineering and acceptable in electrochemical performance.

Further, end of service life indication is the same as that of a standard Li/SVO cell. And, it has been determined that the SVO electrode material and the $CF_x$ electrode material according to the present invention reach end of life at the same time. This is the case in spite of the varied usage in actual defibrillator applications. Since both electrode materials reach end of service life at the same time, no energy capacity is wasted.

The corrosion resistant glass used in the glass-to-metal seals has up to about 50% by weight silicon such as CABAL 12, TA 23, FUSITE 425 or FUSITE 435. The positive terminal leads preferably comprise molybdenum, although titanium, aluminum, nickel alloy, or stainless steel can also be used. The cell casing is an open container hermetically sealed with a lid typically of a material similar to that of the casing.

It is appreciated that various modifications to the inventive concepts described herein may be apparent to those of ordinary skill in the art without departing from the spirit and scope of the present invention as defined by the appended claims.

What is claimed is:

1. An electrochemical cell, which comprises:
a) an anode of an alkali metal;
b) a cathode of a first cathode active material having a relatively low energy density but a relatively high rate capability contacted to outer major sides of a first and a second cathode current collectors and a second cathode active material having a relatively high energy density but a relatively low rate capability contacted to inner major sides of the first and second cathode current collectors, wherein the first cathode active material contacted to the first cathode current collector has a first periphery, the first cathode active material contacted to the second cathode current collector has a second periphery and the second cathode active material contacted to the first and second cathode current collectors has a third periphery greater than each of the first and second peripheries; and
c) an electrolyte activating the anode and the cathode.

2. The electrochemical cell of claim 1 wherein the first and second peripheries are the same, or one is greater than the other.

3. The electrochemical cell of claim 1 wherein the first cathode active material is selected from the group consisting of SVO, CSVO, $V_2O_5$, $MnO_2$, $LiCoO_2$, $LiNiO_2$, $LiMnO_2$, $CuO_2$, $TiS_2$, $Cu_2S$, FeS, $FeS_2$, copper vanadium oxide, and mixtures thereof.

4. The electrochemical cell of claim 1 wherein the second cathode active material is selected from the group consisting of $CF_x$, $Ag_2O$, $Ag_2O_2$, CuF, $Ag_2CrO_4$, $MnO_2$, SVO, and mixtures thereof.

5. The electrochemical cell of claim 1 wherein the first and second cathode current collectors are selected from the group consisting of stainless steel, titanium, tantalum, platinum and gold.

6. The electrochemical cell of claim 1 wherein the first and second cathode current collectors are titanium having a graphite/carbon material coated thereon.

7. The electrochemical cell of claim 1 wherein the anode is lithium, the first cathode active material is SVO, the second cathode active material is $CF_x$ and the first and second cathode current collectors are titanium.

8. The electrochemical cell of claim 1 wherein the alkali metal is in the form of at least one plate contacted to an anode current collector.

9. The electrochemical cell of claim 1 wherein the alkali metal has a serpentine shape weaving between at least two cathode assemblies.

10. The electrochemical cell of claim 1 wherein the first and the second cathode current collectors are connected to a common terminal insulated from a casing for the cell.

11. The electrochemical cell of claim 1 wherein the electrolyte has a first solvent selected from an ester, a linear ether, a cyclic ether, a dialkyl carbonate, and mixtures thereof, and a second solvent selected from a cyclic carbonate, a cyclic ester, a cyclic amide, and mixtures thereof.

12. The electrochemical cell of claim 11 wherein the first solvent is selected from the group consisting of tetrahydrofuran, methyl acetate, diglyme, trigylme, tetragylme, dimethyl carbonate, 1,2-dimethoxyethane, 1,2-diethoxyethane, 1-ethoxy, 2-methoxyethane, ethyl methyl carbonate, methyl propyl carbonate, ethyl propyl carbonate, diethyl carbonate, dipropyl carbonate, and mixtures thereof, and the second solvent is selected from the group consisting of propylene carbonate, ethylene carbonate, butylene carbonate, acetonitrile, dimethyl sulfoxide, dimethyl formamide, dimethyl acetamide, γ-valerolactone, γ-butyrolactone, N-methyl-pyrrolidinone, and mixtures thereof.

13. The electrochemical cell of claim 1 wherein the electrolyte includes a lithium salt selected from the group consisting of $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, LiSCN, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

14. An electrochemical cell, which comprises:
a) an anode comprising lithium;
b) a cathode of silver vanadium oxide contacted to outer major sides of a first and second cathode current collectors and fluorinated carbon contacted to inner major sides of the first and second cathode current collectors, wherein the silver vanadium oxide contacted to the first cathode current collector has a first periphery, the silver vanadium oxide contacted to the second cathode current collector has a second periphery and the fluorinated carbon contacted to the first and second cathode current collectors has a third periphery greater than each of the first and second peripheries; and
c) a nonaqueous electrolyte activating the anode and the cathode.

15. The electrochemical cell of claim 14 wherein the lithium is in the form of at least one plate contacted to an anode current collector.

16. The electrochemical cell of claim 14 wherein the lithium has a serpentine shape weaving between at least two cathode assemblies.

17. The electrochemical cell of claim 14 wherein the cathode current collectors are selected from the group consisting of stainless steel, titanium, tantalum, platinum, gold and nickel.

18. A method powering an implantable medical device, comprising the steps of:
a) providing the medical device;
b) providing an electrochemical cell comprising the steps of:
i) providing an anode of an alkali metal;

ii) providing a cathode of a first cathode active material having a relatively low energy density but a relatively high rate capability contacted to outer major sides of a first and a second cathode current collectors and a second cathode active material having a relatively high energy density but a relatively low rate capability contacted to inner major sides of the first and second cathode current collectors;

iii) including providing the first cathode active material contacted to the first cathode current collector having a first periphery, the first cathode active material contacted to the second cathode current having a second periphery and the second cathode active material contacted to the first and second cathode current collectors having a third periphery greater than each of the first and second peripheries;

iv) activating the anode and cathode with a nonaqueous electrolyte; and c) electrically connecting the electrochemical cell to the medical device.

19. The method of claim 18 including providing the first and second peripheries being the same, or one being greater than the other.

20. The method of claim 18 including connecting the first and second cathode current collectors to a common terminal.

21. The method of claim 18 including providing the alkali metal in the form of at least one plate contacted to an anode current collector.

22. The method of claim 18 including providing the alkali metal having a serpentine shape weaving between at least two cathode assemblies.

23. The method of claim 18 including selecting the first cathode active material from the group consisting of SVO, CSVO, $V_2O_5$, $MnO_2$, $LiCoO_2$, $LiNiO_2$, $LiMnO_2$, $CuO_2$, $TiS_2$, $Cu_2S$, FeS, $FeS_2$, copper vanadium oxide and mixtures thereof.

24. The method of claim 18 including selecting the second cathode active material from the group consisting of $CF_x$, $Ag_2O$, $Ag_2O_2$, CuF, $Ag_2CrO_4$, $MnO_2$, SVO, and mixtures thereof.

25. The method of claim 18 wherein the anode is lithium, the first cathode active material is SVO, and the second cathode active material is $CF_x$.

* * * * *